United States Patent
Woo et al.

(10) Patent No.: US 9,682,149 B2
(45) Date of Patent: Jun. 20, 2017

(54) STABILIZER FOR HYALURONIDASE AND LIQUID FORMULATION COMPRISING HYALURONIDASE

(71) Applicant: BMI KOREA CO., LTD, Jeju (KR)

(72) Inventors: Koo Woo, Gwacheon (KR); Ha-Na Kim, Jeju (KR); Yeong-Jun Baik, Seoul (KR); Sung-Hee Lee, Yongin (KR)

(73) Assignee: BMI KOREA CO., LTD, Jeju-si (KR)

( * ) Notice: Subject to any disclaimer, the term of this patent is extended or adjusted under 35 U.S.C. 154(b) by 0 days.

(21) Appl. No.: 14/435,796

(22) PCT Filed: Aug. 5, 2013

(86) PCT No.: PCT/KR2013/007048
§ 371 (c)(1),
(2) Date: Apr. 15, 2015

(87) PCT Pub. No.: WO2014/069757
PCT Pub. Date: May 8, 2014

(65) Prior Publication Data
US 2015/0283245 A1    Oct. 8, 2015

(30) Foreign Application Priority Data
Nov. 5, 2012    (KR) .................. 10-2012-0124064

(51) Int. Cl.
| | |
|---|---|
| *C12N 9/26* | (2006.01) |
| *A61K 47/34* | (2017.01) |
| *A61K 38/47* | (2006.01) |
| *C12N 9/96* | (2006.01) |
| *A61K 9/00* | (2006.01) |
| *A61K 47/10* | (2017.01) |
| *A61K 47/18* | (2017.01) |

(52) U.S. Cl.
CPC ............ *A61K 47/34* (2013.01); *A61K 9/0019* (2013.01); *A61K 38/47* (2013.01); *A61K 47/10* (2013.01); *A61K 47/183* (2013.01); *C12N 9/2408* (2013.01); *C12N 9/2474* (2013.01); *C12N 9/96* (2013.01); *C12Y 302/01035* (2013.01)

(58) Field of Classification Search
CPC .............. A61K 9/0019; A61K 47/183; C12Y 302/01035
USPC ........................................ 435/201
See application file for complete search history.

(56) References Cited

U.S. PATENT DOCUMENTS

| | | | |
|---|---|---|---|
| 2,795,529 A | 6/1957 | Alburn et al. | |
| 2011/0044977 A1* | 2/2011 | Adler .................. | A61K 9/0019 424/133.1 |
| 2011/0066111 A1 | 3/2011 | Teschner | |

FOREIGN PATENT DOCUMENTS

| | | |
|---|---|---|
| CN | 101970650 | 2/2011 |
| CN | 102065886 | 5/2011 |
| CN | 102573789 | 7/2012 |
| CN | 102655853 | 9/2012 |
| JP | H11-089579 A | 4/1999 |
| JP | 2003-511022 A | 3/2003 |
| JP | 2004-500079 A | 1/2004 |
| JP | 2007-514760 A | 6/2007 |
| JP | 2007-526227 A | 9/2007 |
| JP | 20115-12844 A | 4/2011 |
| JP | 2011-519361 A | 7/2011 |
| KR | 10-2010-013467 | 12/2010 |
| KR | 10-2010-0135291 | 12/2010 |
| KR | 10-2010-0135777 | 12/2010 |
| KR | 10-2012-0105426 | 9/2012 |
| WO | 97/18835 | 5/1997 |
| WO | 2004/092361 | 10/2004 |
| WO | 2009/111066 | 9/2009 |
| WO | 2009/128917 | 10/2009 |

OTHER PUBLICATIONS

Graham et al. Subcellular Fractionation: A Practical Approach, Oxford University Press, (1997) pp. 88-91.*
Kochman, M. Hylenex Accerlerates Time to Peak Blood Concentration for Subcutaneous Morphine; BioPharm International.com (2007) downloaded from http://www.biopharminternational.com/hylenex-accelerates-time-peak-blood-concetration-subcutaneous-morphine on May 10, 2016.*
Extended European Search Report, EPO, Jun. 8, 2016, European Patent Application No. 13852009.3.
SIPO, Search Report, Application No. 2013800576594, no translation, Jan. 9, 2017.
Pharmacist monthly publication vol. 19, No. 3, pp. 163(523)-169(529), 1977.

* cited by examiner

*Primary Examiner* — Scott Long
*Assistant Examiner* — Paul Martin
(74) *Attorney, Agent, or Firm* — Lex IP Meister, PLLC

(57) ABSTRACT

This invention relates to a stable hyaluronidase liquid formulation comprising a hyaluronidase and a stabilizer for hyaluronidase. In particular, the hyaluronidase has a purity of 95% or more and the specific activity of 70,000 IU/mg or more, and the stabilizer for hyaluronidase contains a buffering agent in order to provide pH of 4.0 to 6.0; 0.001 to 0.5 v/v % of a non-ionic surfactant; and 0.1 to 5 mM of a chelating agent or $MgCl_2$. The liquid formulation has advantages in that it stably maintains its activity for a long period of time and may be easily administered than the conventional formulations.

12 Claims, 8 Drawing Sheets

STABILIZER FOR HYALURONIDASE AND LIQUID FORMULATION COMPRISING HYALURONIDASE

CROSS-REFERENCE TO RELATED APPLICATIONS

This application claims the benefit of International Application No. PCT/KR2013/007048 filed on Aug. 5, 2013, which claims the benefit of foreign application KR 10-2012-0124064, filed in Korea on Nov. 5, 2012.

FIELD OF THE INVENTION

The present invention relates to a stable liquid formulation comprising hyaluronidase and a stabilizer for hyaluronidase, which has advantages in that it can stably maintain its enzymatic activity in liquid state for a prolonged period of time and it is simply administered so that it can be usefully utilized.

BACKGROUND OF THE INVENTION

Hyaluronidase, which is a generic term for enzymes of degrading hyaluronic acid, was at first known as a spreading factor by Duran-Reynals but later, as it was observed to exhibit strong activity to hyaluronic acid (HA), it came to be called hyaluronidase (HAase). This enzyme is classified, according to its action mechanism, into hyaluronate 4-glycanohydrolase (EC 3.2.1.35) distributed in testicles, lysosomes, and bee venoms; hyaluronate 3-glycanohydrolase (EC 3.2.1.36) present in leech; and hyaluronate lyase (EC 4.2.2.1) present in bacteria.

In particular, as hyaluronidases (PH-20) in testicles are bonded to a glycosylphosphatidylinositol (GPI) anchor site on the acrosome part of a sperm, they are essential enzymes of causing fertilization by degrading a thick outer wall layer outside ovum. It was known that β (1-4) linkage between N-acetyl-D-glucosamine and D-glucuronic acid present in hyaluronic acid (HA), chondroitin, and chondroitin sulfates is hydrolyzed by the action of PH-20. General molecular formula of these enzymes is $C_{2455}H_{3775}N_{617}O_{704}S_{21}$ and their molecular mass is 53870.9 g/mol. In humans, six genes including HYAL1, HYAL2, HYAL3, and PH-20/SPAM1 are associated with the enzymes.

Since 1950's, the broad applications of the hyaluronidases have been comprehensively reviewed. The first application was the subcutaneous injection of parenteral fluids and besides, they have been used for infiltration and block anesthesia to increase the dispersion of steroids and local anesthetics in orthopedic, ophthalmology, plastic surgery, dental, oral surgery, gynecology, and otolaryngology surgery, and used for dispersion of body fluids not to form agglomeration such as hematoma, prevention of peritoneal adhesion, prevention of calculus formation, and treatment of infertility.

The hyaluronidases currently available on the market are those extracted from ovine testicles and then lyophilized. Such unprocessed hyaluronidases are melted in a suitable concentration, filled into vials and then lyophilized for their manufactures. The thus manufactured hyaluronidases contain excess amounts of foreign proteins. Therefore, the hyaluronidases obtained by the prior methods have not only problems with their stability when converted into a solution but also leave huge problems with their application from a practical perspective because their physiological activity is reduced due to a decrease in their stability over time.

SUMMARY OF THE INVENTION

The inventors have invented the present invention to provide a liquid formulation which substitutes for the prior lyophilized hyaluronidase formulations which have not only problems with their stability when converted into a solution but also leave huge problems with their application from a practical perspective because their physiological activity is reduced due to a decrease in their stability over time.

This invention relates to a liquid formulation containing hyaluronidase, to solve the problems of the prior lyophilized formulations due to their stability and impurities, and the reduction in their physiological activity due to a decrease in their stability over time when prepared into a liquid form from the existing materials.

It is another object of the invention to provide a method of preparing a liquid formulation containing hyaluronidase with improved stability.

It is still another object of the invention to provide a purification method of increasing the purity and stability of hyaluronidase.

It is still another object of the invention to provide a stabilizer for a formulation containing hyaluronidase.

The present invention relates to a liquid formulation containing high purity hyaluronidase and more preferably to a liquid formulation comprising hyaluronidase of which the purity is 95% or more and the specific activity is 70,000 IU/mg or more.

The liquid formulation of the invention may comprise a stabilizer comprising (a) about 1 to 50 mM of a buffering agent to provide pH 4.5 to 6.0, (b) 0.001 to 0.5 v/v % of a non-ionic surfactant, and (c) 0.1 to 5 mM of a chelating agent or alkali metal and alkali earth metal chloride.

Further, the invention relates to a stabilizer of improving the stability of a formulation containing hyaluronidase, preferably high purity hyaluronidase.

The hyaluronidase may be either unpurified hyaluronidase, or purified hyaluronidase. The stabilizer for hyaluronidase according to the present invention contains (a) about 1 to 50 mM of a buffering agent to provides pH 4.5 to 6.0, (b) 0.001 to 0.5 v/v % of a non-ionic surfactant, and (c) 0.1 to 5 mM of a chelating agent or alkali metal and alkali earth metal chloride.

Furthermore, the invention relates to a method of obtaining hyaluronidase with improved purity and stability by purifying a hyaluronidase-containing material with one or more methods selected from the group consisting of affinity chromatography, ion exchange chromatography, and gel filtration.

DETAILED DESCRIPTION OF THE INVENTION

Figure 1:
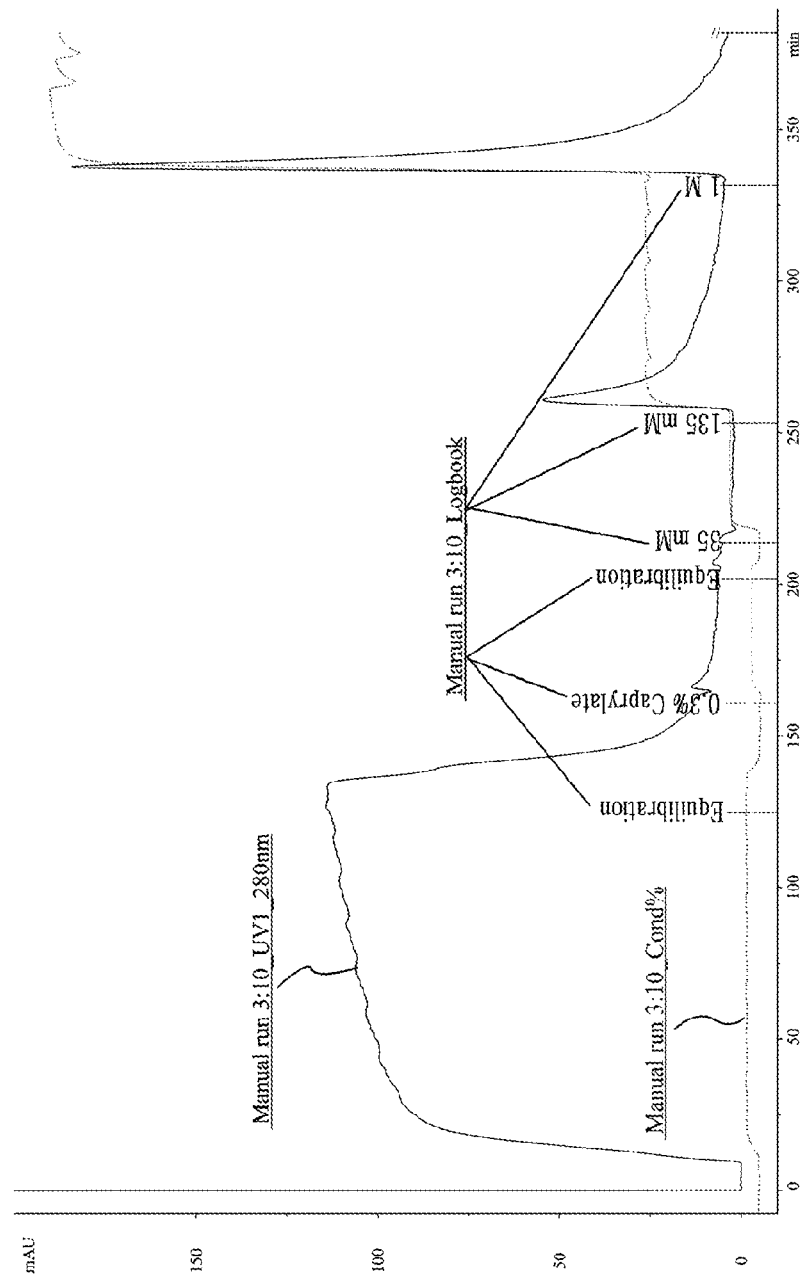
FIG. 1 shows affinity chromatography purification chart using affinity chromatography in which a matrix is composed of cross-linked agarose beads modified with a modified triazine dye (Blue SEPHAROSE™) according to Example 1 of the present invention.

Hereafter, the invention will be described in more detail.

The invention relates to a liquid formulation comprising hyaluronidase of which the purity is 95% or more and the specific activity is 70,000 IU/mg or more.

The hyaluronidases according to the invention may be enzymes commonly derived from testicles of mammals, for example, humans, cows, sheep and pigs. The hyaluronidases commonly available on the market are those obtained by salting out mammalian testicles and then lyophilizing or by depyrogenating after salting-out and then lyophilizing them. For example, a mammalian testicle material which is salted out once and then lyophilized, a testicle material which is salted out twice and then lyophilized, or a testicle material which is salted out twice, depyrogenated and then lyophilized can be used as a source material for purification process. The prior hyaluronidases are extracted through twice salting-out from ovine testicles, lyophilization, dialysis, depyrogenation, and then lyophilization, and those extracted are blended with a large quantity of proteins other than the hyaluronidases.

The lyophilized hyaluronidases available on the market in a crude state include a large quantity of impurities and their purity is thus low, and when prepared into a liquid formulation, their stability is low. Further, the lyophilized formulation is inconvenient because it should be prepared into a liquid form prior to the use thereof. Therefore, there is an urgent need of a liquid formulation comprising hyaluronidase, preferably high purity hyaluronidase with excellent stability.

The hyaluronidase included in the liquid formulation according to the invention comprises hyaluronidase of which the purity is 95% or more and the specific activity is 70,000 IU/mg or more by purifying a crude material of enzymes using one or two more combined methods selected from group consisting of affinity chromatography, ion exchange chromatography, and gel filtration.

The measurement of the activity of the hyaluronidases purified according to the invention is performed by the Assay set forth in "Hyaluronidase for injection" by British Pharmacopoeia Monograph. The stability of the hyaluronidases in this specification can be said to be maintained when the activity (content or specific activity) of hyaluronidases measured according to the Assay set forth in "Hyaluronidase for injection" by British Pharmacopoeia Monograph is at least 90% or more, for example, 90% to 115%, in comparison with their initial activity (100%) which is measured prior to the storage thereof. As for the standards for evaluating the stability, although the Assay in "Hyaluronidase for injection" by British Pharmacopoeia Monograph set forth measurement standard temperature of 37° C., pH 6.4, and time of 20 min. as conditions for measuring the activity of hyaluronidases, measurement in this specification can be performed at a temperature in a range of 36.5° C. to 37.5° C. in a range of pH 6.39 to 6.41 for storage time of 20 min. or so.

The hyaluronidase obtained by performing the purification process according to the present invention guarantees that a protein having high biological enzymatic activity can be obtained. Accordingly, the invention provides a high purity enzyme having such a specific activity that the biological activity of hyaluronidase is 70,000 IU/mg or more, preferably 90,000 IU/mg or more.

The liquid formulation comprising hyaluronidase according to the invention not only secures stability according to the above Assay measurement standards but also can be maintained stably for a prolonged period of time in such a way that the content of the hyaluronidase is maintained 90% or more when stored at a temperature condition of 2 to 8° C. for 0 to 29 weeks.

Further, the highly purified hyaluronidase of the invention has been confirmed to be safe through anaphylactic shock response test and passive cutaneous anaphylaxis reaction test as antigenicity tests using rats.

As for a source material used for the purification method according to the invention, there can be used a material itself separated from mammalian testicles, a product obtained by salting out the material, a product obtained by salting out the material and then depyrogenating it, or a lyophilized form of the material or the product. For example, a mammalian testicle material which is salted out once and then lyophilized, a testicle material which is salted out twice and then lyophilized, or a testicle material which is salted out twice, depyrogenated and then lyophilized can be used as a source material for purification process.

In one embodiment of the purification method according to the invention, the hyaluronidases may be those obtained by purifying the material with affinity chromatography using affinity chromatography in which a matrix is composed of cross-linked agarose beads modified with a modified triazine dye (hereinafter, "Blue SEPHAROSE™"), cation exchange chromatography, anion exchange chromatography, and affinity chromatography using affinity chromatography in which a matrix is composed of cross-linked agarose beads modified with heparin (hereinafter, "heparin SEPHAROSE™"). Preferably, they may be those purified by performing affinity chromatography using Blue SEPHAROSE™, cation exchange chromatography, anion exchange chromatography, affinity chromatography using heparin SEPHAROSE™, and gel filtration.

Preferably, the cation exchange chromatography may be cation exchange chromatography using Mono S or SP SEPHAROSE™ and CM SEPHAROSE™, and the anion exchange chromatography may be anion exchange chromatography using DEAE SEPHAROSE™ or Q SEPHAROSETM™.

The affinity chromatography and the ion exchange chromatography can be performed by ordinary methods and for example, they comprise loading, equilibration, washing, elution, and regeneration processes. As for a solution used for each process, there is an equilibration solution (basic solution), and washing, elution and regeneration solutions, which are prepared by adding other components to the equilibration solution. Preferred examples of the equilibration solution and the washing, elution, and regeneration solutions used for each process are set forth in the following Table.

TABLE 1

Solutions Applicable to Chromatography

| | Type of Buffers | Preferred Ranges |
|---|---|---|
| Affinity Chromatography using Blue SEPHAROSE™ | Equilibration buffer (glycine) | 1~50 mM |
| | Washing buffer (surfactant) | 0.1~0.5 v/v % |
| | Elution buffer (sodium chloride) | 35~200 mM |
| | Buffer pH | pH 8.0~11.0 |
| Cation Exchange Chromatography | Equilibration buffer (sodium phosphate) | 1~50 mM |
| | Equilibration buffer (chelating agent) | 0.1~5 mM |
| | Equilibration buffer (surfactant) | 0.001~0.5% |
| | Elution buffer (sodium chloride) | 35~200 mM |
| | Buffer pH | pH 5.5~6.5 |
| Anion Exchange Chromatography | Equilibration buffer (potassium phosphate) | 1~50 mM |
| | Equilibration buffer (sodium chloride) | 50~100 mM |
| | Buffer pH | pH 6.5~7.5 |
| Affinity Chromatography using Heparin SEPHAROSE™ | Equilibration buffer (sodium acetate) | 1~50 mM |
| | Equilibration buffer (chelating agent) | 0.1~5 mM |
| | Equilibration buffer (surfactant) | 0.001~0.5 v/v % |
| | Elution buffer (sodium chloride) | 200~700 mM |
| | Buffer pH | pH 4.0~5.5 |

For the purification method according to the invention, preferably gel filtration may be performed after chromatography is performed, and examples of the gel filtration may include gel filtrations using sephacryl resin, superdex and superose. In one embodiment of the invention, the gel filtration may be performed by ordinary methods and for example, it may be performed with 1 to 50 mM of sodium acetate, 0.1 to 5 mM of alkali metal or alkali earth metal, 0.001~0.5 v/v % of a non-ionic surfactant and an equilibration solution of pH 4.5~5.5.

In accordance with one embodiment of the invention, the affinity chromatography using Blue SEPHAROSE™ may use equilibration, washing, elution, and regeneration buffers as buffers. Glycine may be used as an equilibration buffer and preferably, 1 to 50 mM of glycine may be used as an equilibration buffer and a preferred pH thereof is 8.0 to 11.0. An ionic surfactant may be used as a washing buffer, preferably it may be used in an amount of 0.1 to 0.5 v/v %, and most preferably it may be used in the amount of 0.3%. Sodium chloride may be used as an elution buffer and preferably, 35 to 200 mM of sodium chloride may be used.

In accordance with one embodiment of the invention, the cation exchange chromatography may use a buffer, and equilibration, elution, and regeneration buffers may be used as the buffers. An equilibration buffer comprising sodium phosphate, a chelating agent and a non-ionic surfactant may be used as the equilibration buffer and preferably, 1 to 50 mM of sodium phosphate, 0.1 to 5 mM of the chelating agent, and 0.001 to 0.5 v/v % of the non-ionic surfactant may be included and a preferred pH thereof is 5.5 to 6.5. Sodium chloride may be used as an elution buffer and most preferably, 35 to 200 mM of sodium chloride may be used.

In accordance with one embodiment of the invention, for the anion exchange chromatography, equilibration, post-loading equilibration, and regeneration buffers may be used as the buffers. Potassium phosphate may be used as an equilibration buffer, preferably, 1 to 50 mM of potassium phosphate may be used, and a preferred pH thereof is 6.5 to 7.5. Sodium chloride may be used as a post-loading equilibration buffer and preferably, 50 to 100 mM of sodium chloride may be used.

In accordance with one embodiment of the invention, for the affinity chromatography using heparin SEPHAROSE™, equilibration, washing, elution, and regeneration buffers may be used as the buffers. An equilibration buffer comprising sodium acetate, a chelating agent and a non-ionic surfactant may be used as the equilibration buffer and preferably, 1 to 50 mM of sodium acetate, 0.1 to 5 mM of the chelating agent, and 0.001 to 0.5 v/v% of the non-ionic surfactant may be used and a preferred pH thereof is 4.0 to 5.5. Sodium chloride may be used as an elution buffer and preferably, 200 to 700 mM of sodium chloride may be used.

The ranges of the specific activities of the enzymes in concentrates obtained after respective purification are shown in the following Table 2.

TABLE 2

| Purification Process | Source Material | $1^{st}$ Purification | $2^{nd}$ Purification | $3^{rd}$ Purification | $4^{th}$ Purification | $5^{th}$ Purification |
|---|---|---|---|---|---|---|
| Specific Activity (IU/mg) | 300-1830 | 7,000-25,000 | 20,000-55,000 | 25,000-75,000 | 50,000-110,000 | 70,000 or higher |

The liquid formulation according to the present invention may be administered via parenteral administration routes and for example, it may be parenterally administered via injection.

The liquid formulation may further comprise sodium chloride and lactose as excipients besides the hyaluronidase, and it may comprise, but not limited to, a pharmaceutically acceptable excipient, diluting agent, etc.

Further, another aspect of the invention relates to a stabilizer for hyaluronidase and in more detail, to a stabilizer comprising about 1 to 50 mM of a buffering agent to provide pH 4.5 to 6.0, 0.001 to 0.5% of a non-ionic surfactant, and 0.1 to 5 mM of a chelating agent or alkali metal and alkali earth metal chloride.

The hyaluronidases to which the stabilizer is applicable may be either unpurified hyaluronidases or purified hyaluronidases and preferably, they are the purified hyaluronidases.

The hyaluronidases may be enzymes commonly derived from testicles of mammals, for example, humans, cows, sheep and pigs, or recombinant hyaluronidases expressed by transducing mammalian-derived hyaluronidases into microbes or animal cells or plant cells. The production methods of the recombinant hyaluronidases are identical to ordinary production methods in microbes, or animal or plant cells according to recombinant methods for mammalian genes, and illustrative methods are described in Frost et al., 1997, BBRC, 236, 10-15; Lin et al., 1993, Proc. Natl. Acad. Sci. USA, 90, 10071-10075; Reitinger et al., 2008, Protein Expression and Purification, 57, 226-233; Kordowicz et al., European patent, WO2000/077221.

The hyaluronidases comprise enzymes obtained by salting out mammalian testicles once and lyophilizing, enzymes obtained by salting out the testicles twice and then lyophilizing, enzymes obtained by salting out the testicles twice, depyrogenating and then lyophilizing, etc. Further, the hyaluronidases may be enzymes purified by one or two more combined methods selected from the group consisting of affinity chromatography, ion exchange chromatography and gel filtration and preferably, they may be hyaluronidases which are purified by the above purification methods and of which the purity is 95% or more and the specific activity is 70,000 IU/mg or more. The purification methods are as described in the above.

For the stabilization of the liquid formulation according to the invention, a pH condition is one of the major factors, and regardless of the buffering agents used therein, the pH is adjusted within values including about 4.0 to about 7.0, preferably, about 4.5 to about 6.0, for examples, values selected from the group consisting of 4.5, 4.7, 5.0, 5.5, 5.7, and 6.0. The pH can be obtained by an adjustment of using an acid or a base known in the pertinent field, or by the use of a suitable mixture of buffering agent components, or by both of them.

The pharmaceutically acceptable buffers suitable for the invention may include, but not limited to, one or more combined buffering agents selected from the group consisting of succinate buffer, acetate buffer, phosphate buffer, citrate buffer, malonate buffer, MES(2-(N-Morpholino)ethanesulphonic acid) buffer, Tris buffer and glycine buffer. A preferred concentration of the buffering agents may be suitably determined in consideration of the intended pH condition of a target solution and the type of the buffering agents to be used and for example, it may be 1 to 50 mM, preferably 10 to 30 mM.

The non-ionic surfactant of the stabilizer may be polyoxyethylene sorbitan fatty acid ester (Tween). For example, it may be those selected from the group consisting of polysorbate 20 (Tween 20), polysorbate 80 (Tween 80) and Triton X-100.

The chelating agent refers to a molecule containing two or more electron donor atoms capable of forming a coordinate bond with a single metal ion and preferably, it may be ethylenediamine tetraacetic acid (EDTA). The concentration of the chelating agent may be 0.1 mM to 5 mM, preferably 0.5 mM to 1 mM.

The alkali metal and alkali earth metal chloride may be $MgCl_2$. The concentration of $MgCl_2$ may be 0.1 mM to 5 mM, preferably 0.5 mM to 5 mM.

Examples of the stabilizer may include $MgCl_2$, a non-ionic surfactant, and a buffering agent to provide pH 4.0 to 6.0, or include EDTA, a non-ionic surfactant, and a buffering agent to provide pH 4.0 to 6.0

The affinity chromatography of the first purification may use a buffer, and equilibration, washing, elution, and regeneration buffers may be used as buffers. Glycine may be used as an equilibration buffer, preferably, 1 to 50 mM of glycine may be used as an equilibration buffer, and a preferred pH thereof is 8.0 to 11.0. An ionic surfactant may be used as a washing buffer, preferably it may be used in an amount of 0.1 to 0.5%, and most preferably it may be used in the amount of 0.3%. Sodium chloride may be used as an elution buffer and preferably, 35 to 200 mM of sodium chloride may be used.

The cation exchange chromatography of the second purification may use a buffer, and equilibration, elution, and regeneration buffers may be used as buffers. The equilibration buffer may include sodium phosphate, EDTA, and Tween 80, preferably, 1 to 50 mM of sodium phosphate, 0.1 to 5 mM of EDTA, and 0.001 to 0.5% of Tween 80 may be included, and a preferred pH thereof is 5.5 to 6.5. Sodium chloride may be used as an elution buffer and most preferably, 35 to 200 mM of sodium chloride may be used.

The anion exchange chromatography of the third purification may use a buffer, and equilibration, post-loading equilibration, and elution buffers may be used as buffers. Potassium phosphate may be used as an equilibration buffer, preferably, 1 to 50 mM of potassium phosphate may be used, and a preferred pH thereof is 6.5 to 7.5. Sodium chloride may be used as a post-loading equilibration buffer and preferably, 50 to 100 mM of sodium chloride may be used.

The affinity chromatography of the fourth purification may use a buffer, and equilibration, washing, elution, and regeneration buffers may be used as buffers. The equilibration buffer may include sodium acetate, EDTA, and Tween 80, preferably, 1 to 50 mM of sodium acetate, 0.1 to 5 mM of EDTA, and 0.001 to 0.5% of Tween 80 may be used, and a preferred pH thereof is 4.0 to 5.5. Sodium chloride may be used as an elution buffer and preferably, 200 to 700 mM of sodium chloride may be used.

The gel filtration of the fifth purification may use a buffer, and an equilibration buffer may be used as a buffer. The equilibration buffer may include sodium acetate, $MgCl_2$, and Tween 80, preferably, 1 to 50 mM of sodium acetate, 0.1 to 5 mM of $MgCl_2$, and 0.001 to 0.5% of Tween 80 may be used, and a preferred pH thereof is 4.5 to 5.5. The liquid formulation refers to any forms of aqueous solutions and any types of suspensions, and it is characterized by being administered via a subcutaneous route.

Since the liquid formulation according to a specific embodiment of the invention can maintain its activity for a prolong period of time in such a way that the content of hyaluronidase is maintained 90% or more even when stored at a temperature condition of 2 to 8° C. for up to 29 weeks, it can solve the prior problem that its physiological activity is reduced due to a decrease in stability over time.

In a specific embodiment of the invention, the purification method of hyaluronidase comprises a step of preparing a source material by extracting from ovine testicles and lyophilizing hyaluronidase; a first purification step of the source material using affinity chromatography using Blue SEPHAROSE™; a second purification step of using cation exchange chromatography after the first purification; a third purification step of using anion exchange chromatography after the second purification; a fourth purification step of using affinity chromatography after the third purification; and a fifth purification step of using gel filtration after the fourth purification, and the types of particular buffers used in each step and preferred ranges thereof are as described with regard to the liquid formulation in the above.

The liquid formulation according to the present invention may be administered via parenteral administration routes and for example, it may be parenterally administered via injection.

The liquid formulation may further comprise sodium chloride and lactose as excipients besides the hyaluronidase, and it may comprise, but not limited to, a pharmaceutically acceptable excipient, diluting agent, etc.

Further, another aspect of the invention relates to a stabilizer for hyaluronidase and in more detail, to a stabilizer comprising about 1 to 50 mM of a buffering agent to provide pH 4.5 to 6.0, 0.001 to 0.5 v/v % of a non-ionic surfactant, and 0.1 to 5 mM of a chelating agent or alkali metal and alkali earth metal chloride.

The hyaluronidases to which the stabilizer is applicable may be either unpurified hyaluronidases or purified hyaluronidases and preferably, they are the purified hyaluronidases.

The hyaluronidases may be enzymes commonly derived from testicles of mammals, for example, humans, cows, sheep and pigs, or recombinant hyaluronidases expressed by transducing mammalian-derived hyaluronidases into microbes or animal cells or plant cells. The production methods of the recombinant hyaluronidases are identical to ordinary production methods in microbes, or animal or plant cells according to recombinant methods for mammalian genes, and illustrative methods are described in Frost et al., 1997, BBRC, 236, 10-15; Lin et al., 1993, Proc. Natl. Acad. Sci. USA, 90, 10071-10075; Reitinger et al., 2008, Protein Expression and Purification, 57, 226-233; Kordowicz et al., European patent, WO2000/077221.

The hyaluronidases comprise enzymes obtained by salting out mammalian testicles once and lyophilizing, enzymes obtained by salting out the testicles twice and then lyophilizing, enzymes obtained by salting out the testicles twice, depyrogenating and then lyophilizing, etc. Further, the hyaluronidases may be enzymes purified by one or two more combined methods selected from the group consisting of affinity chromatography, ion exchange chromatography and gel filtration and preferably, they may be hyaluronidases which are purified by the above purification methods and of which the purity is 95% or more and the specific activity is 70,000 IU/mg or more. The purification methods are as described in the above.

For the stabilization of the liquid formulation according to the invention, a pH condition is one of the major factors, and regardless of the buffering agents used therein, the pH is adjusted within values including about 4.0 to about 7.0, preferably, about 4.5 to about 6.0, for examples, values selected from the group consisting of 4.5, 4.7, 5.0, 5.5, 5.7, and 6.0. The pH can be obtained by an adjustment of using an acid or a base known in the pertinent field, or by the use of a suitable mixture of buffering agent components, or by both of them.

The pharmaceutically acceptable buffers suitable for the invention may include, but not limited to, one or more combined buffering agents selected from the group consisting of succinate buffer, acetate buffer, phosphate buffer, citrate buffer, malonate buffer, MES(2-(N-Morpholino)ethanesulphonic acid) buffer, Tris buffer and glycine buffer. A preferred concentration of the buffering agents may be suitably determined in consideration of the intended pH condition of a target solution and the type of the buffering agents to be used and for example, it may be 1 to 50 mM, preferably 10 to 30 mM.

The non-ionic surfactant of the stabilizer may be polyoxyethylene sorbitan fatty acid ester (Tween). For example, it may be those selected from the group consisting of polysorbate 20 (Tween 20), polysorbate 80 (Tween 80) and Triton X-100.

The chelating agent refers to a molecule containing two or more electron donor atoms capable of forming a coordinate bond with a single metal ion and preferably, it may be ethylenediamine tetraacetic acid (EDTA). The concentration of the chelating agent may be 0.1 mM to 5 mM, preferably 0.5 mM to 1 mM.

The alkali metal and alkali earth metal chloride may be $MgCl_2$. The concentration of $MgCl_2$ may be 0.1 mM to 5 mM, preferably 0.5 mM to 5 mM.

Examples of the stabilizer may include $MgCl_2$, a non-ionic surfactant, and a buffering agent to provide pH 4.0 to 6.0, or include EDTA, a non-ionic surfactant, and a buffering agent to provide pH 4.0 to 6.0

The affinity chromatography of the first purification may use a buffer, and equilibration, washing, elution, and regeneration buffers may be used as buffers. Glycine may be used as an equilibration buffer, preferably, 1 to 50 mM of glycine may be used as an equilibration buffer, and a preferred pH thereof is 8.0 to 11.0. An ionic surfactant may be used as a washing buffer, preferably it may be used in an amount of 0.1 to 0.5 v/v %, and most preferably it may be used in the amount of 0.3%. Sodium chloride may be used as an elution buffer and preferably, 35 to 200 mM of sodium chloride may be used.

The cation exchange chromatography of the second purification may use a buffer, and equilibration, elution, and regeneration buffers may be used as buffers. The equilibration buffer may include sodium phosphate, EDTA, and Tween 80, preferably, 1 to 50 mM of sodium phosphate, 0.1 to 5 mM of EDTA, and 0.001 to 0.5% of Tween 80 may be included, and a preferred pH thereof is 5.5 to 6.5. Sodium chloride may be used as an elution buffer and most preferably, 35 to 200 mM of sodium chloride may be used.

The anion exchange chromatography of the third purification may use a buffer, and equilibration, post-loading equilibration, and elution buffers may be used as buffers. Potassium phosphate may be used as an equilibration buffer, preferably, 1 to 50 mM of potassium phosphate may be used, and a preferred pH thereof is 6.5 to 7.5. Sodium chloride may be used as a post-loading equilibration buffer and preferably, 50 to 100 mM of sodium chloride may be used.

The affinity chromatography of the fourth purification may use a buffer, and equilibration, washing, elution, and regeneration buffers may be used as buffers. The equilibration buffer may include sodium acetate, EDTA, and Tween 80, preferably, 1 to 50 mM of sodium acetate, 0.1 to 5 mM of EDTA, and 0.001 to 0.5% of Tween 80 may be used, and a preferred pH thereof is 4.0 to 5.5. Sodium chloride may be used as an elution buffer and preferably, 200 to 700 mM of sodium chloride may be used.

The gel filtration of the fifth purification may use a buffer, and an equilibration buffer may be used as a buffer. The equilibration buffer may include sodium acetate, $MgCl_2$, and Tween 80, preferably, 1 to 50 mM of sodium acetate, 0.1 to 5 mM of $MgCl_2$, and 0.001 to 0.5% of Tween 80 may be used, and a preferred pH thereof is 4.5 to 5.5. The liquid formulation refers to any forms of aqueous solutions and any types of suspensions, and it is characterized by being administered via a subcutaneous route.

Since the liquid formulation according to a specific embodiment of the invention can maintain its activity for a prolong period of time in such a way that the content of hyaluronidase is maintained 90% or more even when stored at a temperature condition of 2 to 8° C. for up to 29 weeks, it can solve the prior problem that its physiological activity is reduced due to a decrease in stability over time.

In a specific embodiment of the invention, the purification method of hyaluronidase comprises a step of preparing a source material by extracting from ovine testicles and lyophilizing hyaluronidase; a first purification step of the source material using affinity chromatography using Blue SEPHAROSE™; a second purification step of using cation exchange chromatography after the first purification; a third purification step of using anion exchange chromatography after the second purification; a fourth purification step of using affinity chromatography after the third purification; and a fifth purification step of using gel filtration after the fourth purification, and the types of particular buffers used in each step and preferred ranges thereof are as described with regard to the liquid formulation in the above.

In accordance with the high purification method of high purity hyaluronidase according to the invention, the purity of the previously manufactured hyaluronidases can be enhanced.

Further, in accordance with the high purity hyaluronidase injection according to the invention, the stability thereof can be secured by the removal of foreign proteins which are the problems of the previously manufactured hyaluronidases.

Furthermore, the liquid formulation further comprising the stabilizer in addition to the purified hyaluronidase has advantages in that it can stably maintain its activity for a long period of time and it can be simply administered.

Hereafter, the subject invention will be described in more detail with reference to the following examples. However, they are merely to illustrate the invention, and the scope of the invention is not limited by these examples by any means.

EXAMPLE 1

Affinity Chromatography using Blue SEPHAROSE™(first purification)

The materials used for the purification of hyaluronidases in this experiment are, as shown in Table 3 below, 1) a lyophilized material after first salting-out from testicles among the previous processes (the first salted-out material), 2) a lyophilized material after second salting-out (the second salted-out material), and 3) a lyophilized material after depyrogenation (material name: Hyaluronidase (Hdase, below) Shanghai Liamim Co.), and they were used in subsequent 5-step purification methods.

TABLE 3

| | $1^{st}$ Salted-Out Material | $2^{nd}$ Salted-Out Material | Hdase |
|---|---|---|---|
| Content (IU/mg) | About 100~140 | About 360~400 | About 800~1100 |
| Specific Activity (IU/mg of protein) | About 330~470 | About 1,200~1,330 | About 1,330~1,830 |

The chromatography process consists of loading, equilibration, washing, elution and regeneration processes. The first purification used affinity chromatography and buffers used therein are as Table 4 below.

TABLE 4

| Category | Basic Components | Additional Components |
|---|---|---|
| Equilibration buffer (base buffer) | 10 mM Glycine, pH 10.0 | — |
| Washing Buffer | | 0.3% Sodium caprylate |
| Elution Buffer | | 135 mM NaCl |
| Regeneration Buffer | | 1M NaCl |

For the first purification of hyaluronidase, Blue SEPHAROSE™ 6 Fast Flow was used as a resin, and it was used to fill columns with an internal diameter of 1.6 cm until the height of the resin became 10 cm. 1 G of hyaluronidase material was dissolved in 500 mL (2 mg/mL) of equilibration buffer (10 mM Glycine, pH 10.0), and filter remains after filtration was used as a specimen for analysis.

The hyaluronidase specimen was loaded onto the columns, and the loading rate applied was 2.0 mL/min. Thereafter, the columns were equilibrated with the equilibration buffer and washed with a washing buffer (0.3% Sodium caprylate in base buffer). Steps subsequent to the equilibration were analyzed at a flow rate of 3.0 mL/min. After the washing, the resins were equilibrated again with the equilibration buffer and eluted with an elution buffer (135 mM salt in base buffer) to collect solutions that were flowing out. Since the hyaluronidase is very likely to lose its activity in basic condition, the pH of the collected solutions was adjusted to 6.0 to 7.0 by the addition of a pH adjuster, and upon the completion of elution, the columns were regenerated with a regeneration buffer (1 M salt in base buffer). The analysis results are as shown in FIG. 1. The yield and specific activity obtained after the purification are shown in Table 8 below.

EXAMPLE 2

Cation Exchange Chromatography Using Mono S (Second Purification)

Cation exchange chromatography was used as the second purification. Using the buffers set forth in Table 5, specimen loading, equilibration, washing, elution, and regeneration processes were performed.

TABLE 5

| Category | Basic Components | Additional Components |
|---|---|---|
| Equilibration Buffer (base buffer) | 10 mM Sodium phosphate dibasic, 1 mM EDTA, 0.1% Tween 80, pH 6.0 | — |
| Washing Buffer | | 80 mM NaCl |
| Elution Buffer | | 125 mM NaCl |
| Regeneration Buffer | | 1M NaCl |

For the second purification of hyaluronidase, Mono S was used as a resin, and it was used to fill columns with an internal diameter of 1.6 cm until the height of the resin became 10 cm. The specimen firstly purified from Example 1 was diluted by 3 times with an equilibration buffer (10 mM Sodium phosphate dibasic, 1 mM EDTA, 0.1% Tween 80, pH 6.0) and then used as a specimen for analysis.

Figure 2:
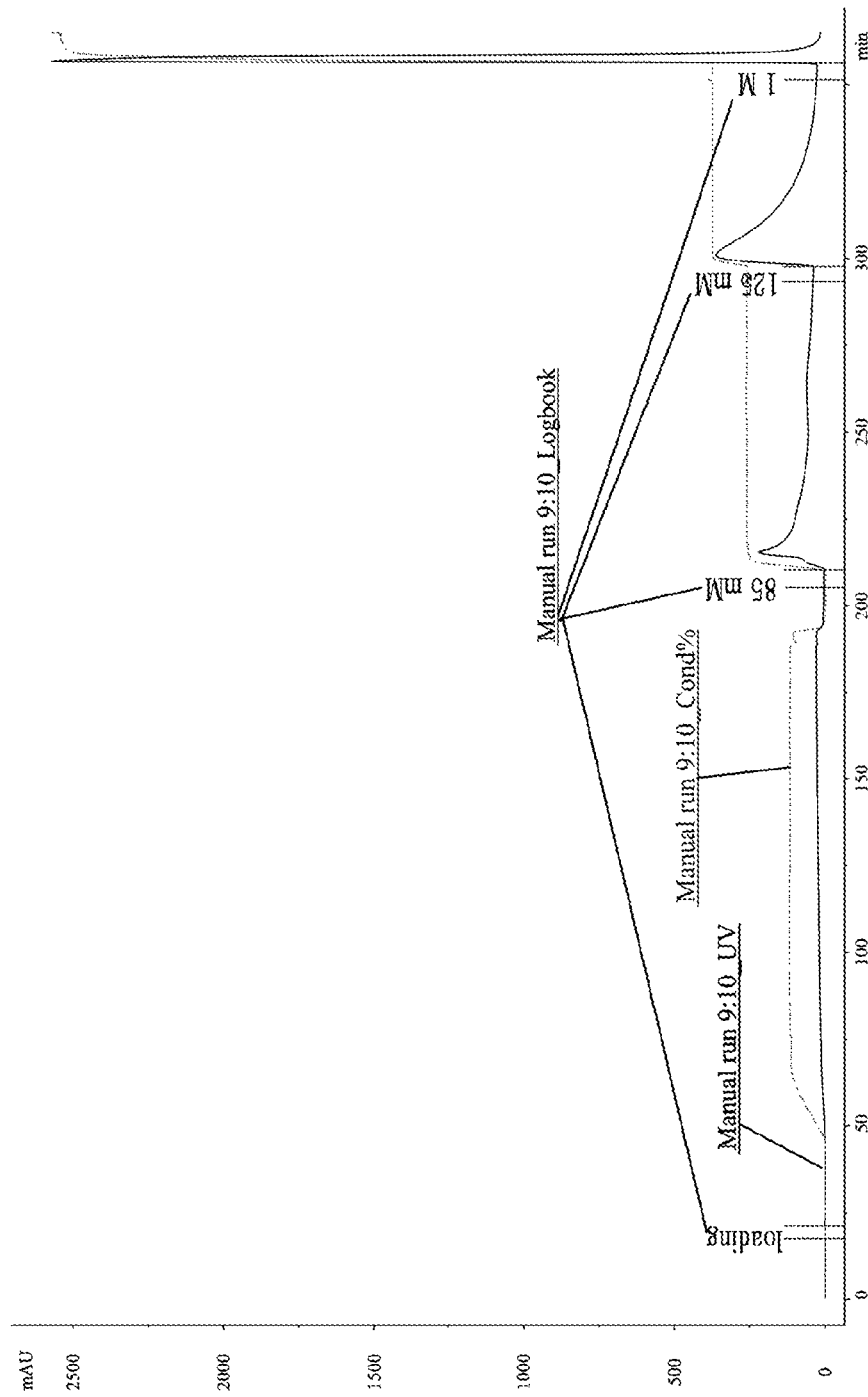
FIG. 2 shows cation exchange chromatography purification chart using Mono S according to Example 2 of the present invention.

The hyaluronidase specimen was loaded onto the columns, and the loading rate applied was 2.0 mL/min. Thereafter, the columns were equilibrated with the equilibration buffer, and steps subsequent to the equilibration were analyzed at a flow rate of 3.0 mL/min. After the equilibration, the resins were washed with a washing buffer (80 mM salt in base buffer). After the washing of the resins, they were eluted with an elution buffer (125 mM salt in base buffer) to collect solutions that were flowing out. Upon the completion of elution, the columns were regenerated with a regeneration buffer (1 M salt in base buffer). The analysis results are as shown in FIG. 2. The yield and specific activity obtained after the purification are shown in Table 8 below.

EXAMPLE 3

Anion Exchange Chromatography using DEAE Sepharese SEPHAROSE™(third purification)

Anion exchange chromatography was used as the third purification. Using the buffers set forth in Table 6, specimen loading, equilibration, and regeneration processes were performed.

TABLE 6

| Category | Basic Components | Additional Components |
|---|---|---|
| Equilibration Buffer (base buffer) | 5 mM Potassium phosphate dibasic, pH 7.1 | — |
| Post-Loading Equilibration Buffer | | 75 mM NaCl |
| Regeneration Buffer | | 1M NaCl |

For the third purification of hyaluronidase, DEAE SEPHAROSE™ was used as a resin, and it was used to fill columns with an internal diameter of 1.6 cm until the height of the resin became 5 cm. The specimen secondly purified from Example 2 was diluted by 1.67 times with an equilibration buffer (5 mM Potassium phosphate dibasic, pH 7.1) and then used as a specimen for analysis.

Figure 3:
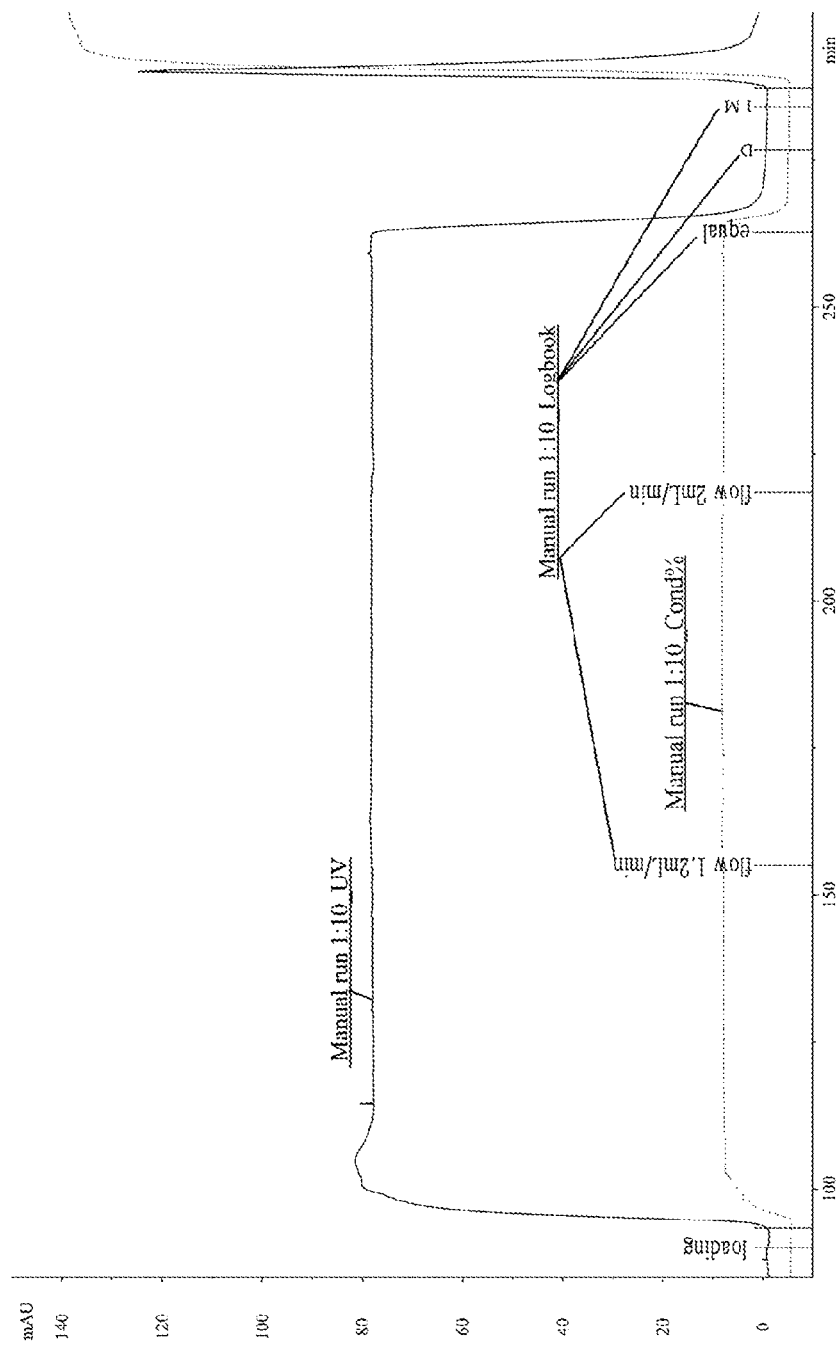
FIG. 3 shows anion exchange chromatography purification chart using DEAE SEPHAROSE™ according to Example 3 of the present invention.

The hyaluronidase specimen was loaded onto the columns, and the loading rate applied was 2.0 mL/min. Thereafter, the columns were equilibrated with a post-loading equilibration buffer (75 mM salt in base buffer), and steps subsequent to the equilibration were analyzed at a flow rate of 3.0 mL/min. After the equilibration, the resins were regenerated with a regeneration buffer (1 M salt in base buffer) without any separate elution step. In the third purification, solutions that were flowing out without being bound to the resins during loading without any separate elution step (flow through (F/T) solution) were deemed to be purified hyaluronidase eluates. The analysis results are as shown in FIG. 3. The yield and specific activity obtained after the purification are shown in Table 8 below.

EXAMPLE 4

Affinity Chromatography using Heparin SEPHAROSE™ (fourth purification)

Affinity chromatography was used as the fourth purification. Using the buffers set forth in Table 7, specimen loading, equilibration, washing, elution, and regeneration processes were performed.

TABLE 7

| Category | Basic Components | Additional Components |
|---|---|---|
| Equilibration Buffer (base buffer) | 20 mM Sodium acetate, 1 mM EDTA, 0.1% Tween 80, pH 4.5 | — |
| Washing Buffer | | 200 mM NaCl |
| Elution Buffer | | 500 mM NaCl |
| Regeneration Buffer | | 1M NaCl |

For the fourth purification of the hyaluronidase thirdly purified by the anion exchange chromatography, Heparin SEPHAROSE™ 6 fast flow was used a resin and it was used to fill columns with an internal diameter of 1.0 cm until the height of the resin became 10 cm. 10× Concentration of an equilibration buffer (200 mM Sodium acetate, 10 mM EDTA, 1.0% Tween 80, pH 4.5) was added to the specimen thirdly purified from Example 3 in 1/9 by volume of the thirdly purified specimen and then used as a specimen for analysis.

Figure 4:
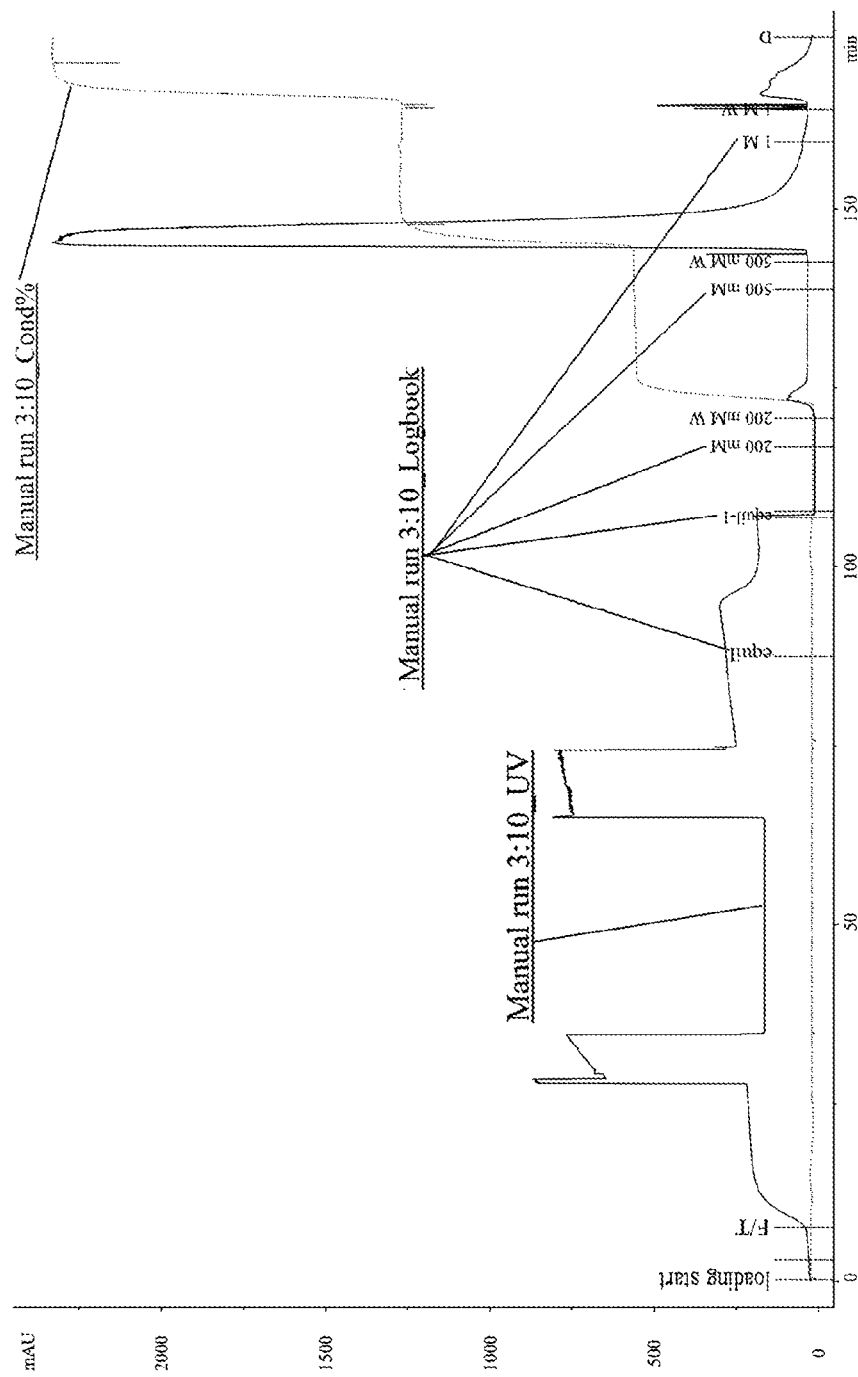
FIG. 4 shows affinity chromatography purification chart using affinity chromatography in which a matrix is composed of cross-linked agarose beads modified with heparin (heparin SEPHAROSE™) according to Example 4 of the present invention.

The hyaluronidase specimen was loaded onto the columns, and the loading rate applied was 0.5 mL/min. Thereafter, the columns were equilibrated with an equilibration buffer (20 mM Sodium acetate, 1 mM EDTA, 0.1% Tween 80, pH 4.5) and washed with a washing buffer (200 mM salt in base buffer). Steps subsequent to the equilibration were analyzed at a flow rate of 1.0 mL/min. After the washing, the resins were eluted with an elution buffer (500 mM salt in base buffer) to collect solutions that were flowing out. Upon the completion of elution, the columns were regenerated with a regeneration buffer (1 M salt in base buffer). The purification chart resultant from this experiment is shown in FIG. 4. The yield and specific activity obtained after the purification are shown in Table 8 below.

EXAMPLE 5

Gel Filtration Using Sephacryl Resin (Fifth Purification)

Gel filtration was used as the fifth purification, and the equilibration solution used therein is a solution containing 10 mM Sodium acetate, 1 mM $MgCl_2$, 0.01% Tween 80, and pH 5.0.

For the fifth purification, by the gel filtration, of the hyaluronidase fourthly purified, Sephacryl S-200 was used a resin and it was used to fill columns with an internal diameter of 1.6 cm until the height of the resin became 90 cm. The specimen solution fourthly purified in Example 4 was concentrated to 1% or so of the resin volume and then used as a specimen for analysis.

The hyaluronidase specimen was loaded onto the columns, and the loading rate applied was 0.1 mL/min. Thereafter, sorting process was performed with an equilibration buffer (10 mM Sodium acetate, 1 mM $MgCl_2$, 0.01% Tween 80, pH 5.0) being flowing out. It was analyzed at a flow rate of 0.1 mL/min, and the solutions that were flowing out by elution were collected. The yield and specific activity obtained after the purification are shown in Table 8 below.

Figure 5:
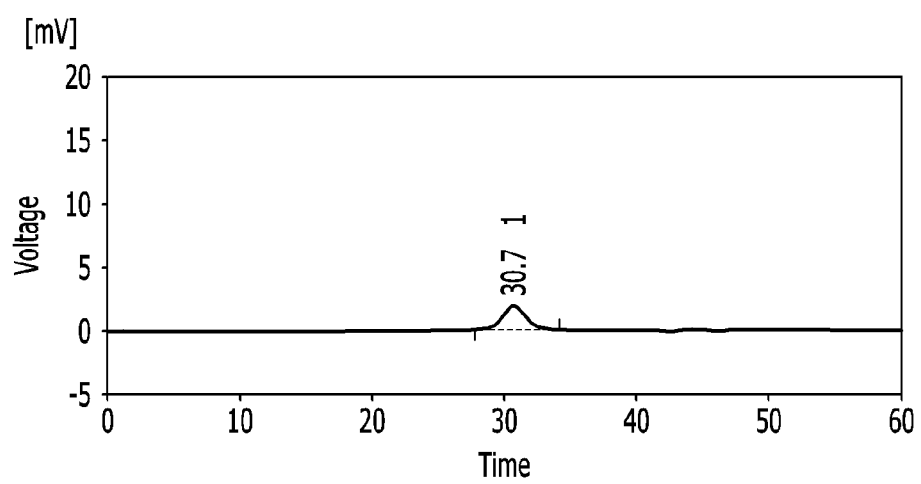
FIG. 5 shows GPC (gel permeation chromatography) analysis after the fifth purification of the first salted-out material according to Example 5 of the present invention.
Figure 6:
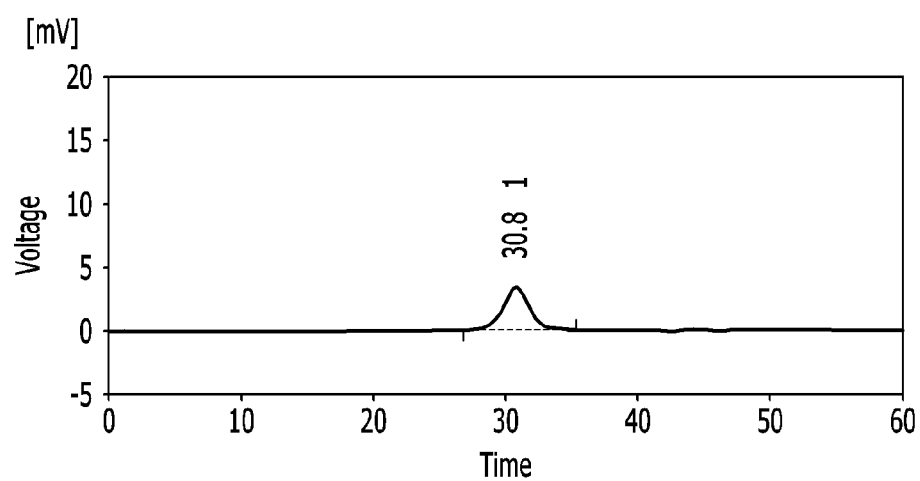
FIG. 6 shows GPC (gel permeation chromatography) analysis after the fifth purification of the second salted-out material according to Example 5 of the present invention.
Figure 7:
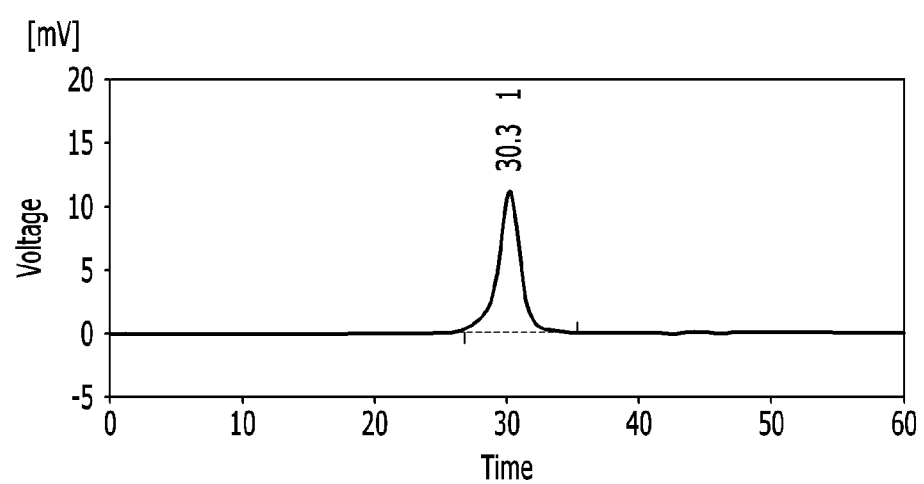
FIG. 7 shows GPC (gel permeation chromatography) analysis after the fifth purification of Hdase material according to Example 5 of the present invention.
Figure 8:
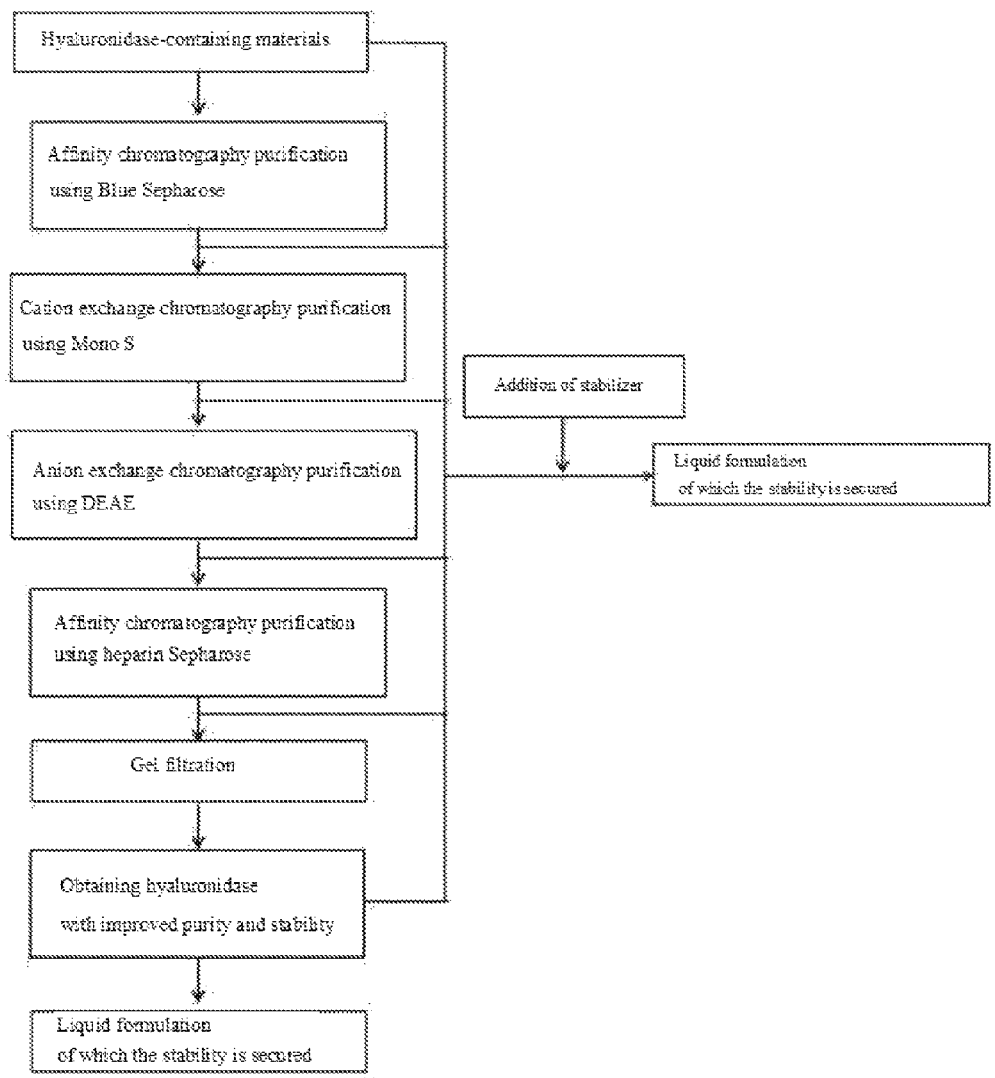
FIG. 8 shows a diagram of the purification method of hyaluronidase and the preparation process for the liquid formulation using unpurified or purified hyaluronidase according to the invention.

The purity test results after the fifth purification with regard to the above three different hyaluronidase specimens are shown in FIGS. 5 to 7 and Table 8. The protein yield set forth in Table 8 refers to the purification yield of all the proteins containing hyaluronidase. As shown in FIGS. 5 to 7, dimers or polymers other than the hyaluronidases are not shown in chromatogram according to the GPC documents after the fifth purification, and the specific activity thereof (IU/mg of protein) was 90,000 IU/mg of protein or more and the purity thereof (GPC) was 95%

TABLE 8

| Purification Process | | Material | $1^{st}$ Purification | $2^{nd}$ Purification | $3^{rd}$ Purification | $4^{th}$ Purification | $5^{th}$ Purification |
|---|---|---|---|---|---|---|---|
| $1^{st}$ Salted-Out Material | Hyaluronidase Content Yield (%) | 100.0 | 87.8 | 78.7 | 73.9 | 72.3 | 33.8 |
| | Protein Yield (%) | 100.0 | 5.2 | 1.3 | 1.3 | 0.7 | 0.2 |
| | Specific Activity (IU/mg) | 408 | 7,649 | 25,965 | 25,615 | 54,612 | 93,664 |

TABLE 8-continued

| Purification Process | | Material | 1st Purification | 2nd Purification | 3rd Purification | 4th Purification | 5th Purification |
|---|---|---|---|---|---|---|---|
| 2nd Salted-Out Material | Hyaluronidase Content Yield (%) | 100.0 | 89.5 | 72.5 | 64.3 | 60.5 | 30.8 |
| | Protein Yield (%) | 100.0 | 6.0 | 1.7 | 1.4 | 0.9 | 0.3 |
| | Specific Activity (IU/mg) | 1,174 | 15,083 | 53,741 | 55,866 | 72,258 | 115,266 |
| Hdase | Hyaluronidase Content Yield (%) | 100.0 | 82.2 | 70.7 | 70.5 | 63.5 | 25.4 |
| | Protein Yield (%) | 100.0 | 5.0 | 1.3 | 1.2 | 0.9 | 0.4 |
| | Specific Activity (IU/mg) | 1,362 | 21,189 | 51,679 | 70,581 | 105,774 | 111,494 |

As shown in FIGS. 5 to 7 and Table 8, it is verified that even when different starting materials (first salted-out material, second salted-out material, and Hdase) were used in the above five-step purification, the specific activity of the final concentrates obtained after the completion of the fifth purification was 90,000 IU/mg of protein or more and the purity thereof was 95% or more. These results mean that whether the hyaluronidase materials of any steps are used, the above results can be achieved through the above five-step purification process and the final concentrates hardly contain dimers or multimers besides the hyaluronidases.

EXAMPLE 6

Stability Test (No Addition of Stabilizer)

6-1: Stability Test of Elution Concentrate after First Purification

The pH of each elution concentrate obtained after the first purification of the first salted-out material, the second salted-out material, and Hdase using affinity chromatography according to Example 1 was adjusted between 6.0 and 7.0 and then, they were dispensed in a certain amount and stored at 4° C. At each point of time, the content of the hyaluronidases was measured and the results are shown in Table 9 below.

At each point of time, the enzyme activity (or content) of the hyaluronidases was tested according to the Assay set forth in "Hyaluronidase for injection" by British Pharmacopoeia Monograph. Throughout the specification, the stability of hyaluronidases refers to the activity (content or specific activity) of hyaluronidases measured according to the Assay set forth in "Hyaluronidase for injection" by British Pharmacopoeia Monograph.

Enzyme activities (or contents) in each test condition are expressed as percent values of specific activity or activity measured at each point of time, with regard to the specific activity or activity at 0 week set forth in Table 8 which is set to 100, and they are shown in Table 9 below.

$$\text{Enzyme Activity Ratio} = \frac{\text{Enzyme Activity at Measurement } (IU/\text{mL})}{\text{Initial Enzyme Activity } (IU/\text{mL})} \times 100$$

TABLE 9

| Elapsed time | 1st Salted-Out Material Enzyme Activity Ratio (%) | 2nd Salted-Out Material Enzyme Activity Ratio (%) | Hdase Enzyme Activity Ratio (%) |
|---|---|---|---|
| 0 week | 100.0 | 100.0 | 100.0 |
| 10 weeks | 100.9 | 101.9 | 112.1 |
| 12 weeks | 98.2 | 99.6 | 103.1 |
| 13 weeks | 100.2 | 98.8 | 100.7 |
| 16 weeks | 99.8 | 102.1 | 103.9 |
| 20 weeks | 100.4 | 100.4 | 113.0 |
| 29 weeks | 100.1 | 99.8 | 109.4 |

As seen in Table 9 above, as a result of content stability test at 4° C. with regard to the elution concentrates obtained by the first purification of the three materials of which the specific activities are different from each other, it was verified that all the three materials showed little reduction in their contents till 29 weeks. The eluates obtained after the first purification were merely adjusted low to have pH 6.0 to 7.0 without any other stabilizers. Meanwhile, the content values exceeding 100% in Table 9, which were obtained from physiological activity measurement such as enzyme activity measurement in comparison with standard products, are considered to be measurement errors which are generated by the broad ranges of test results, as seen in titer tests of biological substances (vaccines, recombinant proteins (cytokine, monoclonal antibody, etc.), toxoid, etc.)

6-2: Stability Test of Low Concentration Solution Obtained by Diluting Elution Concentrate after First Purification The elution concentrates obtained after the first purification of Hdase materials according to Example 1 were diluted to become about 1,500 IU/mL (=100%) and then, dispensed and stored at 4° C. Then, as seen in Table 10 below, the contents thereof were measured at each point of time. The concentration of 1,500 IU/mL is the same as the concentration of the products having hyaluronidases as their material.

Contents at each measurement are expressed as percent values of enzyme activity measured at a specific point of storage time, with regard to the enzyme activity at 0 week which is set to 100%, and shown in Table 10 below. Enzyme specific activity is calculated in accordance with the following mathematical formula:

$$\text{Enzyme Specific Activity } (IU/\text{mg}) = \frac{\text{Enzyme Activity at Measurement } (IU/\text{mL})}{\text{Protein Content Contained in Specimen at Measurement mg/ml}}$$

TABLE 10

| Storage Period | Enzyme Activity Ratio (%) | Enzyme Specific Activity (IU/mg) |
|---|---|---|
| 0 week | 100.0 | 21,103 |
| 10 weeks | 112.0 | 20,568 |
| 12 weeks | 102.8 | 21,033 |
| 13 weeks | 99.6 | 20,968 |
| 16 weeks | 103.2 | 20,869 |
| 20 weeks | 112.1 | 21,153 |
| 29 weeks | 108.7 | 21,532 |

As seen in Table 10 above, the elution concentrates obtained after the first purification showed little reduction in their contents for 29 weeks even at the concentration of 1,500 IU/mL.

Therefore, regardless of the contents of the materials, the concentrates after the first purification of the three materials were stable at 4° C. for 29 weeks and likewise, they were stable at their low concentration (1500 IU/mL) at 4° C. for 29 weeks.

6-3: Stability Test of Elution Concentrate Obtained after One-Step Purification by Second Purification and Fourth Purification Hdase materials were each subject to one step purification of either the second purification or the fourth purification and then, each concentrate was tested with regard to its stability. The second purification and the fourth purification were each performed substantially according to Example 2 and Example 4, and Hdase is a specimen prior to the first purification set forth in Example 1. The storage temperatures of the obtained elution concentrates were set to 4° C., 25° C., and 37° C., respectively and then, the contents of the hyaluronidases were measured at each point of time and their enzyme contents (enzyme activity ratios) were obtained at each point of time as shown in Table 11 below.

TABLE 11

| | Enzyme Activity Ratio (%, Content) | | |
|---|---|---|---|
| Category | | 0 day | 6 days | 20 days |
| $2^{nd}$ Purification Content (%) | 4° C. | 100.0 | 103.4 | 105.8 |
| | 25° C. | 100.0 | 98.2 | 99.3 |
| | 37° C. | 100.0 | 101.9 | 102.2 |
| $4^{th}$ Purification Content (%) | 4° C. | 100.0 | 104.1 | 91.0 |
| | 25° C. | 100.0 | 91.0 | 85.4 |
| | 37° C. | 100.0 | 95.3 | 81.5 |

Further, in order to investigate the content ranges of the hyaluronidases when stored for a long period of time, the concentrates obtained by performing the second purification were stored at 4° C. for 29 weeks and at each point of time, the contents of the hyaluronidases were measured. The results are shown in Table 12 below.

TABLE 12

| Days | Enzyme Activity Ratio (%) | Enzyme Specific Activity (IU/mg) |
|---|---|---|
| 0 week | 100.0 | 12,647 |
| 10 weeks | 100.1 | 12,423 |
| 12 weeks | 103.6 | 12,856 |
| 13 weeks | 97.7 | 12,498 |
| 16 weeks | 98.3 | 12,563 |
| 20 weeks | 103.0 | 12,893 |
| 29 weeks | 98.8 | 12,143 |

As seen in Table 11 and Table 12, in addition to the concentrates after the first purification, the concentrates purified once by the second purification were stable at 4° C. for 29 weeks.

EXAMPLE 7

Conditions of Stabilizer

The concentrates used for the stabilizer condition tests were hyaluronidases having a purity of 95% or more which were the products obtained after the fifth purification of Hdase material in Example 5, which were then adjusted to a concentration 1,500 IU/mL (=100%) and used to prepare solutions according to the conditions set forth in Tables, respectively.

7-1: Stabilization Components

The hyaluronidase having a purity of 95% or more was adjusted to 1,500 IU/mL (=100%) and used to prepare solutions according to the conditions set forth in Table 13 below, which were then stored at 4° C. and tested to measure the contents of hyaluronidases at each point of time. As a result, there was a reduction in contents, as seen in Table 13 below.

TABLE 13

| | | | Metal | | | Enzyme Activity Ratio | |
|---|---|---|---|---|---|---|---|
| Nos. | EDTA | $MgCl_2$ | Salts | Tween 80 | pH | 0 week | 1 week |
| 1 | — | — | — | — | 5.0 | 100 | 60.4 |
| 2 | — | — | — | — | 7.0 | 100 | 53.0 |
| 3 | 1 mM | — | — | — | 5.0 | 100 | 47.6 |
| 4 | — | 1 mM | — | — | 5.0 | 100 | 52.1 |
| 5 | — | — | — | 0.10% | 5.0 | 100 | 65.5 |
| 6 | — | — | — | 0.01% | 5.0 | 100 | 54.7 |
| 7 | — | — | NaCl (150 mM) | 0.01% | 5.0 | 100 | 71.7 |
| 8 | — | — | $CaCl_2$ (1 mM) | 0.01% | 5.0 | 100 | 66.6 |
| 9 | — | — | MnCl2 (1 mM) | 0.01% | 5.0 | 100 | 74.1 |

* Basic Buffer: 10 Mm Sodium acetate

The same hyaluronidases were adjusted to 1,500 IU/mL (=100%) and used to prepare solutions according to the conditions of Table 14 below, which were then stored at 4° C. and tested to measure the contents of hyaluronidases at each point of time. The results of Table 15 were thus obtained.

TABLE 14

| Category | EDTA/$MgCl_2$ | Surfactant | pH |
|---|---|---|---|
| Condition 1 | 1 mM EDTA | 0.01 v/v % Tween 80 | pH 4.5 |
| Condition 2 | 1 mM EDTA | 0.01 v/v % Tween 80 | pH 5.0 |
| Condition 3 | 1 mM EDTA | 0.01 v/v % Tween 80 | pH 6.0 |
| Condition 4 | 1 mM $MgCl_2$ | 0.01 v/v % Tween 80 | pH 4.5 |
| Condition 5 | 1 mM $MgCl_2$ | 0.01 v/v % Tween 80 | pH 5.0 |
| Condition 6 | 1 mM $MgCl_2$ | 0.01 v/v % Tween 80 | pH 6.0 |

TABLE 15

| | Enzyme Activity Ratio (%) | | | | |
|---|---|---|---|---|---|
| Conditions | 0 week (%) | 3 weeks (%) | 4 weeks (%) | 14 weeks (%) | 23 weeks (%) |
| Condition 1 | 100 | 103.8 | 102.9 | 103.9 | 104.6 |
| Condition 2 | 100 | 103.9 | 96.9 | 98.8 | 99.8 |

TABLE 15-continued

| | Enzyme Activity Ratio (%) | | | | |
|---|---|---|---|---|---|
| Conditions | 0 week (%) | 3 weeks (%) | 4 weeks (%) | 14 weeks (%) | 23 weeks (%) |
| Condition 3 | 100 | 103 | 102.1 | 103.6 | 104.2 |
| Condition 4 | 100 | 100.5 | 99.8 | 101.5 | 101.2 |
| Condition 5 | 100 | 99.1 | 98.9 | 105.2 | 106 |
| Condition 6 | 100 | 101.3 | 101.8 | 103.6 | 102.3 |

From the above results, it was verified that stabilization components for hyaluronidase are combined conditions of EDTA or $MgCl_2$+Tween 80+pH 4.5 to 6.0.

7-2: Stabilizer Concentration Conditions

The hyaluronidases used in stability test were those purified over 95%, and the test concentration was adjusted to 1,500 IU/mL (=100%). The conditions set forth in Table 16 below were used for preparation, and stability test was performed. The concentrations of EDTA, $MgCl_2$, and Tween 80 were diluted two times and ten times, and stability test was performed at storage conditions of 4° C. and 25° C.

TABLE 16

| Category | EDTA/$MgCl_2$ | Tween 80 | pH | Storage Temperature |
|---|---|---|---|---|
| Condition 1 | 0.5 mM EDTA | 0.005% | 5.0 | 4° C. |
| Condition 2 | 0.1 mM EDTA | 0.001% | 5.0 | 4° C. |
| Condition 3 | 0.5 mM $MgCl_2$ | 0.005% | 5.0 | 4° C. |
| Condition 4 | 0.1 mM $MgCl_2$ | 0.001% | 5.0 | 4° C. |
| Condition 5 | 0.5 mM EDTA | 0.005% | 5.0 | 25° C. |
| Condition 6 | 0.1 mM EDTA | 0.001% | 5.0 | 25° C. |
| Condition 7 | 0.5 mM $MgCl_2$ | 0.005% | 5.0 | 25° C. |
| Condition 8 | 0.1 mM $MgCl_2$ | 0.001% | 5.0 | 25° C. |

The test results are shown in Table 17 below.

TABLE 17

| | Enzyme Activity Ratio (%) | | | | | | |
|---|---|---|---|---|---|---|---|
| Content (%) | 0 week | 3 weeks | 6 weeks | 10 weeks | 15 weeks | 20 weeks | 26 weeks |
| Condition 1 | 100.0 | 99.3 | 99.5 | 99.6 | 97.7 | 98.9 | 98.6 |
| Condition 2 | 100.0 | 100.4 | 99.6 | 97.3 | 76.3 | 67.8 | 61.8 |
| Condition 3 | 100.0 | 100.5 | 100.4 | 100.7 | 96.0 | 100.4 | 100.7 |
| Condition 4 | 100.0 | 99.1 | 102.4 | 102.8 | 72.0 | 75.6 | 71.1 |
| Condition 5 | 100.0 | 98.7 | 90.8 | 83.8 | 70.3 | 59.9 | 57.1 |
| Condition 6 | 100.0 | 93.3 | 75.1 | 62.2 | 57.9 | 50.9 | 51.8 |
| Condition 7 | 100.0 | 98.5 | 113.0 | 93.9 | 68.5 | 67.2 | 60.5 |
| Condition 8 | 100.0 | 96.8 | 77.6 | 66.6 | 57.7 | 71.0 | 56.1 |

As seen in the above Table, the hyaluronidases were stable for about 26 weeks under condition 1 and condition 3, and its stability showed a decreased tendency under the other conditions.

EXAMPLE 8

8.1: Stabilizer Test for Hdase Specimen

With regard to unpurified Hdase specimen of which the first purification was not even performed, set forth in Example 1, its stability was tested with EDTA or $MgCl_2$+Tween 80+pH 5.0. After the specimen (Hyaluronidase, Content about 800~1100 IU/mg) used in the existing hyaluronidase products was dissolved in buffers or water for injection (WFI), respectively, set forth in Table 18 below to become 1,500 IU/mL (=100%), its stability test was performed at storage conditions of 4° C., 25° C., and 37° C.

TABLE 18

Buffer 1  5 mM Sodium acetate, 1 mM EDTA, 0.01% Tween 80, pH 5.0
Buffer 2  5 mM Sodium acetate, 1 mM $MgCl_2$, 0.01% Tween 80, pH 5.0

The test results are shown in Table 19 below.

TABLE 19

| | Enzyme Activity Ratio (%) | | | | | |
|---|---|---|---|---|---|---|
| Content (%) | Storage Temperature | 0 day | 2 days | 6 days | 20 days | 37 days | 60 days |
| Buffer 1 | 4° C. | 100.0 | 99.3 | 94.4 | 98.4 | 99.9 | 100.8 |
| | 25° C. | 100.0 | 102.3 | 106.9 | 87.6 | 88.5 | 90.1 |
| | 37° C. | 100.0 | 88.2 | 47.9 | 6.1 | 1.1 | — |
| Buffer 2 | 4° C. | 100.0 | 98.8 | 105.0 | 103.9 | 109.1 | 103.2 |
| | 25° C. | 100.0 | 106.1 | 99.5 | 97.4 | 94.5 | 100.3 |
| | 37° C. | 100.0 | 90.4 | 74.0 | 32.9 | 16.9 | 2.2 |
| WFI | 4° C. | 100.0 | 90.3 | 78.6 | 50.6 | 37.6 | 21.8 |
| | 25° C. | 100.0 | 90.3 | 68.6 | 41.6 | 20.3 | 4.3 |
| | 37° C. | 100.0 | 45.7 | 25.9 | 3.9 | 0.9 | — |

As seen in Table 19 above, the materials dissolved in WFI showed a rapid reduction in contents when compared to the materials dissolved in other buffers (EDTA or $MgCl_2$+Tween 80+pH 5.0), and it can be concluded from this result that the composition of EDTA or $MgCl_2$+Tween 80+pH 5.0 contributes the stability of hyaluronidases (4° C.).

8-2: Stabilizer Test for Purified Concentrates According to Examples 2 to 5

Each concentrate obtained from each step which was performed in sequence according to Examples 2 to 5 was diluted to 1,500 IU/mL (=100%) using the equilibration buffer of each purification step, and the stability test thereof was performed at storage conditions of 4° C. and 37° C. The results are shown in Table 20 below.

TABLE 20

| | Enzyme Activity Ratio (%) | | | | | |
|---|---|---|---|---|---|---|
| Category | Storage Temperature | 0 day | 9 days | 20 days | 37 days | 60 days |
| Ex. 2 | 4° C. | 100.0 | 103.3 | 101.3 | 99.6 | 99.6 |
| | 37° C. | 100.0 | 100.9 | 102.5 | 100.8 | 101.3 |
| Ex. 3 | 4° C. | 100.0 | 103.0 | 97.3 | 96.8 | 94.6 |
| | 37° C. | 100.0 | 102.3 | 99.4 | 97.6 | 90.3 |
| Ex. 4 | 4° C. | 100.0 | 99.1 | 100.1 | 102.3 | 101.1 |
| | 37° C. | 100.0 | 99.6 | 99.8 | 100.0 | 98.6 |
| Ex. 5 | 4° C. | 100.0 | 102.6 | 100.4 | 99.4 | 103.2 |
| | 37° C. | 100.0 | 100.8 | 99.6 | 97.3 | 98.8 |

As seen in Table 20, the contents of hyaluronidases were not reduced during the observation period.

8-3: Stability Test of Specimens Obtained after Removing EDTA/MgCl$_2$ by Dialysis from Concentrates Obtained after Purification According to Examples 2 to 5

In order to investigate the stabilization effects of EDTA or MgCl$_2$ after the removal thereof when they were used for purification steps, each concentrate obtained after the purification according to Examples 2 to 5 was diluted to 1,500 IU/mL (=100%), they were dialyzed using a buffer from which EDTA/MgCl$_2$ was removed set forth in Table 21 below. After that, the stability test thereof was performed at storage conditions of 4° C. and 37° C., and the results are shown in Table 22 below. At both 4° C. and 37° C., the contents were reduced.

TABLE 21

| | Buffer Composition for dialysis |
|---|---|
| 2$^{nd}$ Purification | 10 mM Sodium phosphate dibasic, 0.1% Tween 80, pH 5.0 |
| 3$^{rd}$ Purification | 5 mM Potassium phosphate dibasic, pH 5.0 |
| 4$^{th}$ Purification | 20 mM Sodium acetate, 0.1% Tween 80, pH 5.0 |
| 5$^{th}$ Purification | 10 mM Sodium acetate, 0.01% Tween 80, pH 5.0 |

TABLE 22

| | | Enzyme Activity Ratio (%) | | |
|---|---|---|---|---|
| Category | Storage Temperature | 0 day | 9 days | 20 days |
| 2$^{nd}$ Purification | 4° C. | 100.0 | 84.8 | 67.9 |
| | 37° C. | 100.0 | 73.4 | 48.7 |
| 3$^{rd}$ Purification | 4° C. | 100.0 | 81.8 | 63.7 |
| | 37° C. | 100.0 | 53.2 | 28.1 |
| 4$^{th}$ Purification | 4° C. | 100.0 | 87.7 | 69.0 |
| | 37° C. | 100.0 | 77.4 | 39.3 |
| 5$^{th}$ Purification | 4° C. | 100.0 | 80.9 | 67.3 |
| | 37° C. | 100.0 | 71.9 | 47.5 |

With regard to high purity hyaluronidases, no problems occurred in anaphylactic shock response and passive cutaneous anaphylaxis reaction test using rats, so the stability thereof was secured. Therefore, the high purity hyaluronidase has merits as an injection in that its purity is higher than those injections currently available on the market and it has excellent stability.

What is claimed is:

1. A hyaluronidase liquid formulation comprising:
   (i) a hyaluronidase having the purity of 95% or more and the specific activity of 70,000 IU/mg or more; and
   (ii) a stabilizer of hyaluronidase consisting of
      a buffering agent to provide pH 4.0 to 6.0,
      0.001 to 0.5 v/v % of a non-ionic surfactant, and
      0.1 to 5 mM of a chelating agent or MgCl$_2$.

2. The hyaluronidase liquid formulation of claim 1, wherein the liquid formulation is an injectable formulation.

3. The hyaluronidase liquid formulation of claim 1, wherein the liquid formulation has a stability to maintain the activity of the hyaluronidase up to 90% or more with regard to its initial enzymatic activity at a temperature condition of 2 to 8° C.

4. The hyaluronidase liquid formulation of claim 1, wherein the hyaluronidase is an active component of the formulation.

5. The hyaluronidase liquid formulation of claim 4, where the chelating agent is EDTA.

6. The hyaluronidase liquid formulation of claim 4, wherein the non-ionic surfactant is selected from the group consisting of polyoxyethylene-sorbitan fatty acid ester and Triton X-100.

7. The hyaluronidase liquid formulation of claim 6, wherein the non-ionic surfactant is selected from the group consisting of polysorbate 20, and polysorbate 80.

8. The hyaluronidase liquid formulation of claim 4, wherein the buffering agent is selected from the group consisting of succinate buffer, acetate buffer, phosphate buffer, citrate buffer, malonate buffer, 2-(N-Morpholino)ethanesulphonic acid(MES) buffer, Tris buffer and glycine buffer.

9. The hyaluronidase liquid formulation of claim 1, wherein the hyaluronidase is a recombinant hyaluronidase produced by transducing a mammalian hyaluronidase gene into microbes, animal cells or plant cells, or is an extract derived from sheep, cows, pigs, or humans.

10. The hyaluronidase liquid formulation of claim 1, wherein the hyaluronidase is purified from a hyaluronidase-containing material by one or more methods selected from the group consisting of affinity chromatography, ion exchange chromatography, and gel filtration.

11. The hyaluronidase liquid formulation of claim 10, wherein the affinity chromatography is affinity chromatography in which a matrix is composed of cross-linked agarose beads modified with a modified triazine dye, or affinity chromatography in which a matrix is composed of cross-linked agarose beads modified with heparin.

12. The hyaluronidase liquid formulation of claim 10, wherein the hyaluronidase is purified by sequentially using all of the following chromatography methods in order: (1) affinity chromatography in which a matrix is composed of cross-linked agarose beads modified with a modified triazine dye, (2) cation exchange chromatography, (3) anion exchange chromatography, and (4) affinity chromatography in which a matrix is composed of cross-linked agarose beads modified with heparin.

* * * * *